US008629317B2

(12) United States Patent
Cogne et al.

(10) Patent No.: US 8,629,317 B2

(45) Date of Patent: Jan. 14, 2014

(54) NON-HUMAN TRANSGENIC MAMMAL FOR THE CONSTANT REGION OF THE CLASS A HUMAN IMMUNOGLOBULIN HEAVY CHAIN AND APPLICATIONS THEREOF

(75) Inventors: Michel Cogne, Isle (FR); Christophe Sirac, Limoges (FR); Micael Bardel, Couzeix (FR); Catherine Decourt, Rilhac-Rancon (FR); Caroline Le Morvan, Vicq-sur-Breuil (FR)

(73) Assignees: Centre National de la Recherche Scientifique, Paris Cedex (FR); Universite de Limoges, Limoges Cedex (FR)

( * ) Notice: Subject to any disclaimer, the term of this patent is extended or adjusted under 35 U.S.C. 154(b) by 1415 days.

(21) Appl. No.: 10/577,061

(22) PCT Filed: Oct. 21, 2004

(86) PCT No.: PCT/FR2004/002701

§ 371 (c)(1), (2), (4) Date: Feb. 27, 2007

(87) PCT Pub. No.: WO2005/047333

PCT Pub. Date: May 26, 2005

(65) Prior Publication Data

US 2007/0248601 A1 Oct. 25, 2007

(30) Foreign Application Priority Data

Oct. 24, 2003 (FR) ..................................... 03 12502

(51) Int. Cl.

*A01K 67/027* (2006.01)
*C12N 15/74* (2006.01)
*C12P 21/00* (2006.01)

(52) U.S. Cl.

USPC ........... 800/13; 424/93.21; 435/320.1; 800/4; 800/8; 800/21

(58) Field of Classification Search

None

See application file for complete search history.

(56) References Cited

U.S. PATENT DOCUMENTS 5,545,807 A 8/1996 Surani et al.
5,714,352 A * 2/1998 Jakobovits .................... 435/462
7,547,817 B2 * 6/2009 Green et al. .................... 800/18

FOREIGN PATENT DOCUMENTS

WO WO 02/059154 8/2002

OTHER PUBLICATIONS

Qiu et al. Intl Immunol 1999;11:37-46.*
GeneBank AC073553 (Sep. 2002).*
Moreadith et al., J. Mol. Med. 1997;75(3):208-16.*
Mullins et al. Journal of Clinical Investigation, 1996.*
Denning, Nat Biotech 2001;19:559-562.*
Yanagimachi, Mol Cell Endocrinol 2002;187:241-8.*
Wilmut, Cloning Stem Cell 2003;5:99-100.*
Polejaeva et al, Nature 2000;407:86.*
Harriman et al. J Clin Invest 1996;97-477-85.*
Luby et al. J Exp Med 2001;193:159-68.*
Wall, Cloning Stem Cells 2001;3:209-220.*
Scinicariello et al. Immunol 2001;103:441-8.*
XP-011182522 "Localization of the 3' IgH Locus Elements that Effect Long-Distance Regulation of Class Switch Recombination" by Eric Pinaud et al., Immunity, vol. 15, 187-199, Aug. 2001.
XP-0011182373 Research Report "Production of Antigen-Specific Human Monoclonal Antibodies: Comparison of Mice Carrying IgH/κ or IgH/κ/λ Transloci" by S. Magadán et al., BioTechniques vol. 33, No. 3 pp. 680-690, Sep. 2002.
"Insertion of the IgH locus 3' regulatory palindrome in expression sectors warrants sure and efficient expression in stable B cell transfectants" by Christine Chauveau et al., Gene 222 (1998) 279-285.
"Use of a simple, general targeting vector for replacing the DNA of the heavy chain constant region in mouse hybridoma cells" by Diana Ronai et al., Journal of Immunological Methods 275 (2003) 191-202.
XP-002319762 "Immunoglobulin class-switch recombination in mice devoid of any Sμ tandem repeat" by Ahmend Amine Khamlichi et al., Blood, May 15, 2004, vol. 103, No. 10, pp. 3828-3836.

* cited by examiner

*Primary Examiner* — Janice Li

(74) *Attorney, Agent, or Firm* — William E. Beaumont

(57) ABSTRACT

The invention relates to a non-human transgenic mammal with an IgH locus modified by replacement of the switching sequence Sμ with all or part of a transgene comprising the gene Cα of a class A human immunoglobulin, including at least the exon, coding for the CH3 domain and the membrane exon and the applications of the above for the production of humanized class IgA antibodies.

22 Claims, 8 Drawing Sheets

Figure 1:
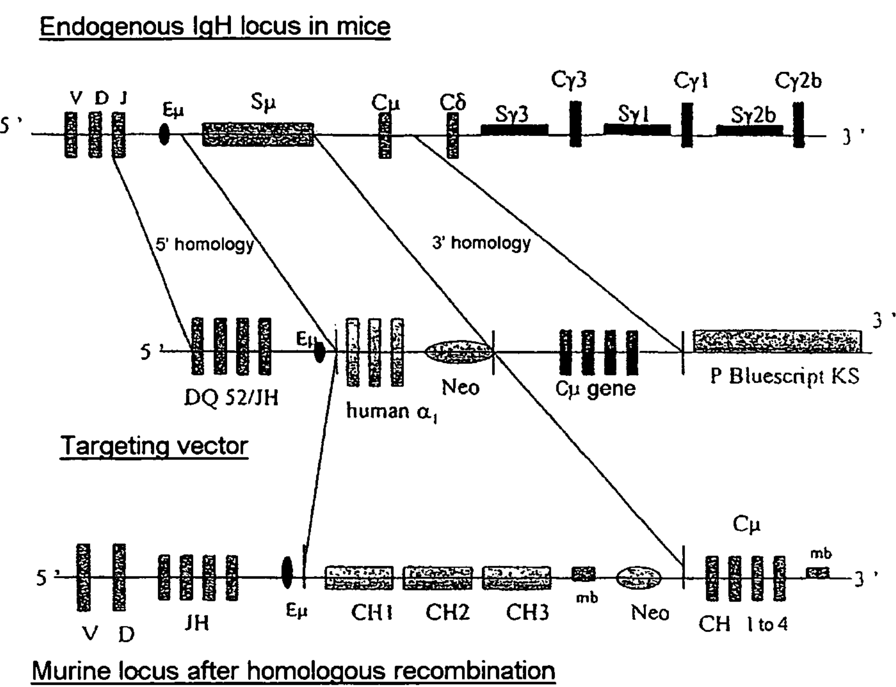

NON-HUMAN TRANSGENIC MAMMAL FOR THE CONSTANT REGION OF THE CLASS A HUMAN IMMUNOGLOBULIN HEAVY CHAIN AND APPLICATIONS THEREOF

RELATED APPLICATIONS

The present application is based on, and claims priority from French Patent Application Number 0312502, filed Oct. 24, 2003, the disclosure of which is hereby incorporated by reference herein in its entirety.

The present invention relates to non-human mammal transgenic for the constant region of the class A human immunoglobulin heavy chain and to its applications for the production of humanized class IgA antibodies.

The class A immunoglobulins (IgA) comprise two identical heavy chains of isotype α1 (subclass IgA1) or α2 (subclass IgA2) in humans, combined via disulfide bridges with two identical light chains of isotype kappa (κ) or lambda (λ).

The α heavy chain, which is specific to this class of immunoglobulins, exists in membrane form and in secreted form. The secreted form comprises four domains of about 110 amino acids: a variable domain VH and three constant domains CH1, CH2 and CH3, and a hinge (H) region between CH2 and CH3 and a C-terminal octapeptide. The penultimate cysteine of this octapeptide can form a covalent bond with the J chain (or joining piece) which serves to combine two IgA heavy chains so as to form dimeric IgAs. The membrane form additionally comprises a hydrophobic domain allowing anchoring of the protein in the membrane, and an intracytoplasmic domain. The region of the heavy chain corresponding to the CH1, CH2, H and CH3 domains combined either with the C-terminal octapeptide (secreted form) or with the hydrophobic and intracytoplasmic domain (membrane form) is called constant region by contrast to the region corresponding to the variable domain VH which is called variable region.

The κ and λ light chains, which are common to all the classes and subclasses of immunoglobulins, comprise two domains: a variable domain (VL) and a constant domain (CL). In humans, the expression of the κ and λ chains is equivalent, whereas in mice, the expression of the λ locus is very low such that 95% of the light chains are of the κ type. The region of the light chain corresponding to the CL domain is called constant region by contrast to the region corresponding to the variable domain VL, which is called variable region.

The immunoglobulin genes are organized into loci, one locus for the heavy chains (IgH locus) and one locus for each of the light chains (lambda and kappa loci).

The loci of the light chains each comprise V and J genes encoding the variable domain and C genes encoding the constant domain; during the differentiation of the B lymphocytes, a V gene is rearranged with a J gene and a C gene, and the V region is additionally subjected to somatic mutations which make it possible to produce antibodies with high affinity for the antigen.

The locus of the heavy chains comprises V, D and J genes encoding the variable domain and C (Cμ, Cδ, Cγ, Cϵ and Cα) genes encoding the constant domains of the isotypes of the different classes of immunoglobulins; each C gene, except Cδ, is preceded by a switch (S) sequence. The Cα (Cα1 and Cα2 in humans) genes contain introns separating the exons encoding the constant domains CH1, CH2 and CH3 and the membrane (mb) exon; the sequence encoding the hinge region is included in the exon cH2. During the differentiation of the B lymphocytes, a V gene is rearranged with a D gene and a J gene, and the V region is also subjected to somatic mutations which make it possible to produce antibodies with high affinity for the antigen. In addition, while the primary response to the antigen mainly consists of IgM, the secondary response is associated with the class switch mechanism during which the switch sequence Sμ, situated upstream of Cμ recombines with another switch sequence, thus leading to the production of another class of immunoglobulin (IgG, IgE or IgA).

The diversity of the antibodies produced in response to the stimulation by an antigen results from the combination of several mechanisms: the multiplicity of the V genes, the somatic mutation of these V genes, the somatic recombination of the V genes and the somatic recombination of the switch sequences.

The IgAs exist in the body in two different forms: a serum IgA and a secretory IgA (s-IgA).

The serum IgA represents 15 to 20% of the serum immunoglobulins; more than 80% of the human serum IgA is in monomeric form, whereas in most other mammalian species it is essentially in dimeric form.

The secretory IgA constitutes the main immunoglobulin in secretions (ocular, salivary, mammary, tracheobronchial and urogenital secretions), where it exists in the form of an IgA dimer combined with another protein, the secretory component, which is probably coiled around the IgA dimer and attached by disulfide bridges to the CH2 domain of each IgA monomer. Unlike the J chain, the secretory piece is not synthesized by the plasmocytes but by the epithelial cells. The dimeric IgA secreted by the subepithelial plasmocytes binds to the poly-Ig receptors present at the basal pole of the epithelial cells. The s-IgA/receptor complex is then endocytosed and transported through the cell while remaining attached to the membrane of the transport vesicles. The latter fuse with the plasma membrane at the luminal surface and release the dimeric IgA combined with the secretory piece which results from the cleavage of the receptor. Thus, the secretory piece facilitates the transport of the IgAs in the secretions and protects them from proteolysis.

Because of their capacity to cross the epithelium of the mucous membranes and to prevent the entry of pathogens such as viruses, bacteria, parasites and toxins, the IgAs play a major role in local immunity: ocular, respiratory, digestive and urogenital immunity. The mode of action of the IgAs encompasses active mechanisms (complement activation, binding to the Fc receptor) and passive mechanisms (blocking of the receptors for pathogens (viruses) and inhibition of the motility of bacteria). A close correlation between a specific IgA response and protection against an infection has been demonstrated, in particular for viruses (rotavirus, influenza virus, poliovirus, cytomegalovirus, respiratory syncytial virus, Epstein-Barr virus). Class IgA protective antibodies directed against numerous human pathogens (HIV, influenza A virus, bacteria, toxins, parasites) have been isolated.

Because of this special property, IgAs have specific applications for the diagnosis and treatment of infectious diseases and cancer. They could be used in passive immunotherapy to neutralize pathogens (serotherapy). They could also be used in active immunotherapy (vaccination) as vector to target tumor antigens or antigens of pathogenic microorganisms in the mucous membranes, so as to induce local immunity specific to these antigens. In addition, they are useful as reliable, safe, stable and well-defined reagent for the diagnosis of diseases such as celiac disease, as a replacement for human IgAs (antitransglutaminase, antiendomysium or antigliadin IgA) obtained from patients, which expose technicians to risks of transmission of human pathogens (virus, prion).

However, the development of these applications is limited because there is no effective method for producing recombinant human or humanized class IgA antibodies.

The expression humanized antibody is understood to mean an antibody derived from a non-human mammal by fusion of the constant domains of the heavy and light chains of a human antibody with the variable domains of the heavy and light chains of an antibody from a non-human mammal.

Indeed, the methods for producing recombinant human or humanized antibodies which are currently available have the following disadvantages:

the in vitro methods are based on the simultaneous expression, from one or more recombinant vectors, of antibody heavy and light chains, of a J chain and optionally of a secretory piece; the heavy and light chains comprise the variable domains of the heavy and light chains (VH and VL) of a human or murine monoclonal antibody of interest, fused respectively with the constant domains CH1, CH2 and CH3 of a heavy chain α, and Cλ or Cκ of a human light chain, or the VH and VL domains are fused with a CH3 domain including the C-terminal octapeptide (International Applications PCT WO 98/30577 and PCT WO 99/54484). For example International Application PCT WO 98/30577 describes the in vitro production, with the aid of one or more recombinant baculoviruses, of recombinant human dimeric mini-IgAs (IgA-J) comprising the VH and VL domains of a murine or human monoclonal antibody, each fused with a CH3 domain including the C-terminal octapeptide, combined by means of a J chain; only one recombinant mini-IgA directed against the HIV gp120, obtained from a class IgG1 neutralizing human monoclonal antibody (S1-1 antibody), is described.

These methods, which are specific to IgAs, are limited to murine antibodies and to a few rare human antibodies for which hybridomas have been isolated.

the in vivo methods are based on the production of human monoclonal immunoglobulins from genetically modified mice possessing a transgene consisting of:

the complete IgH locus and the locus of the kappa light chain, in their germinal configuration, (PCT Application WO 02/059154, Mendez et al., Nature Genetics, 1997, 15, 146-156; Green and Jakobovits, J. Exp. Med., 1998, 188, 483-495 and American Patent U.S. application Ser. No. 08/759,620), a mini-IgH locus comprising one or more VH, DH and JH genes, the Cμ gene and a second gene for the constant region, preferably for the Cγ region, and the locus of the kappa light chain (PCT Application WO 02/059154, U.S. Pat. No. 5,545,807), and the complete IgH locus and the locus of the lambda chain in its germinal configuration (American Patent U.S. application Ser. No. 09/734,613). Said mice are optionally genetically disabled for the endogenous kappa locus (κ−/− mice) and optionally possess a mutation which inactivates the endogenous IgH locus (μMT −/− mutation).

These methods do not make it possible to produce large quantities of human class IgA immunoglobulins.

Surprisingly, the inventors have constructed transgenic mouse lines which produce large quantities of humanized class IgA immunoglobulins (in the gram per liter range in mice). The antibodies produced by these animals are predominantly humanized IgAs; they do not contain IgM and only very small quantities of other classes of immunoglobulins (IgG and IgE).

Consequently, the subject of the invention is a non-human transgenic mammal, characterized in that it comprises an IgH locus modified by replacing the switch sequence Sμ with all or part of a transgene consisting of the Cα gene for a human class A immunoglobulin, including at least the exon encoding the CH3 domain and the membrane exon.

In accordance with the invention, the Cα transgene or the part of this transgene including at least the exon encoding the CH3 domain and the membrane exon, which is inserted in place of the switch sequence Sμ, is therefore located between the intronic activator Eμ, in 5' and the Cμ gene in 3' (FIG. 1).

In this construct, the suppression of the switch sequence Sμ associated with the insertion of the Cα transgene in place of this sequence, abolishes the expression of the endogenous μ gene responsible for the synthesis of heavy IgM chains. In addition, that of the other genes for the immunoglobulin heavy chains is greatly reduced because of the blocking of the class switch toward the immunoglobulin constant genes located downstream of Cμ on the endogenous IgH locus. Thus, the transgenic animals obtained produce large quantities of chimeric IgAs in which the constant domain of the heavy chain is humanized and the variable domains are of murine origin.

The human transgenic α heavy chain benefits from a completely diversified repertoire since it corresponds to the normal repertoire generated by the rearrangements of the VH, D and JH segments of the murine IgH locus. In addition, the transgenic animals are capable of producing antibodies with high affinity as a secondary response to the antigen since their B lymphocytes can recruit the somatic hypermutation phenomenon.

According to an advantageous embodiment of the invention, said non-human transgenic mammal is homozygous for said modified IgH locus.

According to another advantageous embodiment of the invention, said IgH locus is modified by replacing the switch sequence Sμ with the entire Cα gene, including the CH1, CH2, CH3 and mb exons, separated by the corresponding introns.

According to another advantageous embodiment of the invention, said IgH locus is modified by replacing the switch sequence Sμ with the segment of the Cα gene including the exon encoding the CH3 domain and the membrane exon.

According to another advantageous embodiment of the invention, said Cα gene is Cα1.

According to yet another advantageous embodiment of the invention, said non-human transgenic mammal comprises another transgene encoding a human immunoglobulin light chain.

According to an advantageous feature of this embodiment, said light chain is a kappa chain.

Preferably, said transgene is a human kappa gene comprising the intronic activator Eμ upstream and the palindrome hs3a/hs1,2/hs3b downstream. These sequences, which are described in Chauveau et al., Gene, 1998, 222, 279-285, make it possible to obtain a high expression of the human kappa chain in B cells and to induce the somatic hypermutation of the human kappa transgene. Preferably, said transgene is under the control of the promoter of the human heavy chain (pVH).

According to another advantageous feature of this embodiment, said non-human transgenic mammal is dizygous for said transgene.

According to an advantageous feature of the preceding embodiments of the invention, said non-human transgenic mammals comprising another transgene encoding a human kappa light chain possess an endogenous locus of the immunoglobulin kappa light chain inactivated (deleted or mutated) in particular by homologous recombination. Preferably, said non-human transgenic mammals are homozygous for said inactivation; preferably, they are transgenic mice. Among the non-human transgenic mammals in which the endogenous locus of the immunoglobulin kappa light chain has been inactivated by homologous recombination, there may be mentioned in particular the mouse line described in Zou et al., EMBO J., 1993, 12, 811-820.

Such non-human transgenic mammals produce humanized IgAs in which practically all the light chains are of human origin.

According to another advantageous feature of the preceding embodiments of the invention, said non-human mammals transgenic for the α1 heavy chain and optionally for the human kappa light chain possess an endogenous locus of the J chain inactivated (deleted or mutated) in particular by homologous recombination. Preferably, said non-human transgenic mammals are homozygous for said inactivation; preferably, they comprise another transgene encoding a human J chain; more preferably still, they are transgenic mice. Such non-human transgenic mammals are humanized both for the production of IgA and for a protein which combines with the IgAs, the J chain.

The invention encompasses transgenic animals obtained from any mammalian species.

According to another advantageous embodiment of the invention, said non-human transgenic mammal is a transgenic mouse.

The invention encompasses in particular a double-transgenic mouse line, called HAMIGA line for "Humanized Antibodies Made Up Of Monoclonal Immunoglobulin A", comprising:

- an IgH locus modified by replacing the switch sequence Sμ with the Cα1 gene for a human class A immunoglobulin, and
- a complete Vκ gene comprising the rearranged VκI gene with a Jκ5 gene, the Jκ-Cκ intron and the Cκ gene, under the transcriptional control of the promoter of the human heavy chain (pVH), the intronic activator Eμ upstream and the palindrome hs3a/hs1,2/hs3b downstream.

The animals of this double-transgenic line produce IgAs that are partially humanized for the heavy chain and completely humanized as regards the light chain.

Indeed, the expression of the transgenic kappa chain in this line is capable of causing allelic exclusion, that is to say of preventing, in most transgenic B cells, the expression of the endogenous genes for murine immunoglobulin light chains.

The repertoire of response to the antigens of this mouse line is normal given that it is mainly the VH domain of the heavy chain which contributes to the formation of the antibody site. Now, the human transgenic α heavy chain benefits from a completely diversified repertoire since it corresponds to the normal repertoire generated by the rearrangements of the VH, D and JH segments of the murine IgH locus, as specified above.

In addition, the mice of this transgenic line are capable of producing antibodies with high affinity as a secondary response to the antigen since their B lymphocytes can recruit the somatic hypermutation phenomenon both at the level of the gene for the heavy chain and the transgene for the kappa light chain.

The transgenic animals according to the invention are obtained by conventional methods for animal transgenesis, according to the standard protocols as described in *Transgenic Mouse: Methods and Protocols; Methods in Molecular Biology*, Clifton, N.J., Volume 209, October 2002, edited by: Marten H. Hofker, Jan Van Deursen, Marten H. Hofker and Jan Van Deursen, published by Holly T. Sklar: Humana Press.

The sequences of the human and murine genes for immunoglobulins which serve for the construction of the transgenic animals according to the invention are known and accessible in databases. For example, the sequence of CH1, CH2 and CH3 exons and of the membrane exon of the human Cα1 gene correspond to the accession numbers J00220 and M60326, respectively, in the Genbank/EMBL database.

The construction of the Vκ gene is as described in Chauveau et al., Gene, 1998, 222, 279-285; the sequence of the rearranged VκI gene with the Jκ5 gene and the Cκ gene corresponds to the sequence having the accession number X64133 in the EMBL/Genbank database, which encodes a human light chain having the sequence corresponding to the accession number CAA45494 in the EMBL database.

The insertions of gene fragments into the genome of non-human mammals may be carried out in a random manner, preferably they are carried out in a targeted manner, by homologous recombination with an appropriate targeting vector optionally comprising recombination sequences of a site-specific recombinase such as the LoxP sites of the Cre recombinase. The inactivations or deletions of gene fragments in the genome of non-human mammals are carried out by homologous recombination with an appropriate targeting vector optionally comprising recombination sequences of a site-specific recombinase such as the LoxP sites of the recombinase. The double-transgenic animals are obtained by crossing animals transgenic for the alpha heavy chain with animals transgenic for the light chain, as defined above. The double-transgenic animals are optionally crossed with transgenic animals in which the endogenous locus of the immunoglobulin kappa light chain has been inactivated by homologous recombination and/or with animals in which the endogenous locus of the immunoglobulin J chain has been inactivated and which additionally possess a human J transgene, as defined above.

The subject of the present invention is also a homologous recombination targeting vector, characterized in that it comprises the Cα gene for a human class A immunoglobulin or a segment of this gene including at least the exon encoding the CH3 domain and the membrane exon, flanked by fragments of sequences of the IgH locus from a non-human mammal which are adjacent to the Sμ sequence.

According to an advantageous embodiment of said targeting vector, it comprises a cassette for expressing an appropriate selection marker, adjacent to said Cα gene or to the segment of said gene as defined above.

According to an advantageous feature of this embodiment, said expression cassette is flanked by site-specific recombination sequences. Preferably, said sequences are LoxP sequences of the Cre recombinase. This feature optionally makes it possible to excise said expression cassette.

According to another embodiment of said targeting vector, said fragments of sequences which are adjacent to the Sμ sequence are of murine origin.

According to another embodiment of said targeting vector, the C.alpha. gene or the segment of said gene is flanked in 5' by a fragment of about 5 kb corresponding to the JH/E.mu. region and in 3' by a fragment of about 5 kb corresponding to the C.mu. region, said fragments consisting of the sequences SEQ ID NO: 7 and 8 corresponding respectively to positions 131281 to 136441 and 140101 to 145032 in the sequence of murine chromosome 12 (accession number AC073553 in the EMBL/GenBank database).

The subject of the present invention is also embryonic cells of a non-human mammal, modified by a targeting vector as defined above.

Said modified embryonic cells (totipotent stem cells) are useful for the production of transgenic mammals as defined above; they are injected into mammalian blastocysts, according to conventional animal transgenesis techniques.

The subject of the present invention is also the use of a non-human transgenic mammal as defined above for the production of humanized class IgA antibodies or fragments of these antibodies.

The subject of the present invention is also a method for preparing humanized class IgA antibodies or fragments of these antibodies, characterized in that it comprises at least the following steps:

the immunization of a non-human transgenic mammal as defined above with an antigen of interest, the production, by any appropriate means, of humanized class IgA antibodies or fragments of these antibodies, from serum, secretions or B lymphocytes of said non-human transgenic mammal sacrificed beforehand.

The non-human transgenic mammals according to the invention have the advantage of allowing the production of class IgA monoclonal antibodies which are immediately humanized class IgA chimeric antibodies. The method of producing humanized class IgA monoclonal antibodies according to the invention is therefore more simple, more rapid and more economical than the prior art methods since it does not require additional steps of cloning the genes for said antibodies and of fusing the variable domains of said antibodies with the constant domains of human immunoglobulins.

The invention encompasses the production of polyclonal or monoclonal antibodies consisting of monomeric or dimeric IgAs and of s-IgAs, and fragments thereof, in particular the Fab, Fab'2 and Fc fragments.

The humanized class IgA antibodies as defined above and fragments thereof are prepared by conventional techniques known to persons skilled in the art, such as those described in *Antibodies: A Laboratory Manual*, E. Howell and D. Lane, Cold Spring Harbor Laboratory, 1988.

More precisely:

the polyclonal antibodies are prepared by immunizing a non-human transgenic mammal as defined above with an antigen of interest, optionally coupled to KLH or to albumin and/or combined with an appropriate adjuvant such as Freund's (complete or incomplete) adjuvant or aluminum hydroxide; after obtaining a satisfactory antibody titer, the antibodies are harvested by collecting serum from immunized animals and enriched with IgA by precipitation, according to conventional techniques, and then the specific IgAs are optionally purified by affinity chromatography on an appropriate column to which the antigen is attached as defined above, so as to obtain a preparation of monospecific IgAs.

the monoclonal antibodies are produced from hybridomas obtained by the fusion of B lymphocytes from a non-human transgenic mammal as defined above with myelomas, according to the Köhler and Milstein technique (Nature, 1975, 256, 495-497); the hybridomas are cultured in vitro, in particular in fermenters or produced in vivo, in the form of ascites; alternatively, said monoclonal antibodies are produced by genetic engineering as described in American U.S. Pat. No. 4,816,567. For example, non-human transgenic mammals as defined above are immunized strongly and repeatedly with chosen antigens (bacterial, viral or fungal antigens, tumor-specific antigens such as the carcinoembryonic antigen, and the like), according to a standard protocol comprising a first immunization by intraperitoneal injection of the antigen in an equivalent volume of Freund's complete adjuvant and then a second immunization (booster) 15 days later under identical conditions but, this time, with Freund's incomplete adjuvant. The monoclonal antibodies are produced according to a standard protocol comprising sacrificing the animals two weeks after the last booster, removing the spleen, suspending the splenic lymphocytes and fusing these lymphocytes with the SP2/0 cell line (this murine line does not produce any murine antibody, is immortalized, and possesses the entire secretion machinery necessary for the secretion of immunoglobulins).

the antibody fragments are produced from cloned $V_H$ and $V_L$ regions, from mRNAs for hybridomas and for splenic lymphocytes of an immunized non-human transgenic mammal according to the invention; for example, the Fv and Fab fragments are expressed at the surface of filamentous phages according to the Winter and Milstein technique (Nature, 1991, 349, 293-299); after several selection steps, the antibody fragments specific for the antigen are isolated and expressed in an appropriate expression system, by conventional techniques for cloning and expression of recombinant DNA.

The antibodies or fragments thereof as defined above are purified by conventional techniques known to persons skilled in the art, such as affinity chromatography.

The subject of the present invention is also a humanized class IgA antibody capable of being obtained by the method as defined above, characterized in that it comprises a chimeric heavy chain in which the constant domain(s) are of human origin and a human light chain in which the variable domain is encoded by VκI-Jκ5.

The invention encompasses the humanized class IgA antibodies in which the light chain is encoded by the VκI-Jκ5 gene having the EMBL/Genbank sequence X64133 or a sequence produced by hypermutation of this sequence, in particular after activation of B lymphocytes in the presence of the antigen.

The subject of the present invention is also a fragment of a humanized class IgA antibody capable of being obtained by the method as defined above, characterized in that it comprises a fragment of said heavy and light chains as defined above.

The invention encompasses polyclonal antibodies, monoclonal antibodies and fragments thereof (Fab, Fc, Fab'2).

The humanized antibodies according to the invention and fragments thereof as defined above are well tolerated in humans (minimization of the risk of allergic reaction by interspecies immunization) and have a prolonged half-life in humans, given that the constant region of the heavy chain and the entire light chain of these antibodies are of human origin.

The subject of the present invention is also a medicament comprising a humanized class IgA antibody or a fragment of this antibody, as defined above; such an antibody or its fragment is used in particular in passive immunotherapy (serotherapy) for the prevention and treatment of an infectious disease or cancer.

The subject of the present invention is also an immunogenic or vaccine composition, characterized in that it comprises at least one humanized class IgA antibody and a fragment of this antibody, as defined above, combined with an antigen, preferably in the form of an antigen-antibody complex comprising a humanized class IgA antibody or a fragment of this antibody directed against said antigen; such a composition makes it possible both to target the antigen to the epithelium of the mucous membranes and to protect it from proteolysis.

The subject of the present invention is also a pharmaceutical composition, characterized in that it comprises at least one humanized class IgA antibody or a fragment of this antibody, as defined above, combined by any appropriate means with an active ingredient; such a composition makes it possible both to target the active ingredient to the epithelium of the mucous membranes and to protect it from proteolysis.

According to an advantageous embodiment of the compositions according to the invention, they additionally contain at least one pharmaceutically acceptable vehicle and optionally carrier substances and/or adjuvants.

The pharmaceutically acceptable vehicles, the carrier substances and the adjuvants are those conventionally used.

The adjuvants are advantageously chosen from the group consisting of oily emulsions, saponin, inorganic substances, bacterial extracts, aluminum hydroxide and squalene.

The carrier substances are advantageously selected from the group consisting of unilamellar liposomes, multilamellar liposomes, miscelles of saponin or solid microspheres of a saccharide or auriferous nature.

The compositions according to the invention are administered by the general route (oral, intramuscular, subcutaneous, intraperitoneal or intravenous) or by the local route (ocular, nasal, vaginal, rectal); the dose and the rate of administration vary according to the species (human or animal) and the disease to be treated.

The subject of the present invention is also a diagnostic reagent comprising a humanized class IgA antibody or a fragment of this antibody, as defined above.

The subject of the present invention is also the use of a humanized class IgA antibody or a fragment of this antibody, as defined above, for the preparation of a medicament intended for the prevention and treatment of infectious diseases and cancer.

The subject of the present invention is also the use of a humanized class IgA antibody or a fragment of this antibody, as defined above, for the preparation of a reagent intended for the diagnosis of infectious diseases and cancer.

In addition to the preceding features, the invention also comprises other features which will emerge from the description which follows, which refers to examples of production and use of non-human transgenic mammals according to the present invention and to the appended drawings in which:

FIG. 1 illustrates the structure of the modified IgH locus obtained by homologous recombination between the murine IgH locus and the targeting vector called p-alpha1KI, comprising a 5.5 kb fragment of the human alpha 1 gene including three exons encoding the constant domains CH1, CH2 and CH3 and the membrane (mb) exon and a neo cassette bordered by LoxP sites (1.6 kb fragment), flanked upstream by a fragment of about 5 kb corresponding to the JH-Eμ region (DQ 52/JH fragment) and downstream by another fragment of about 5 kb corresponding to the Cμ gene (Cμ fragment).

Figure 2:
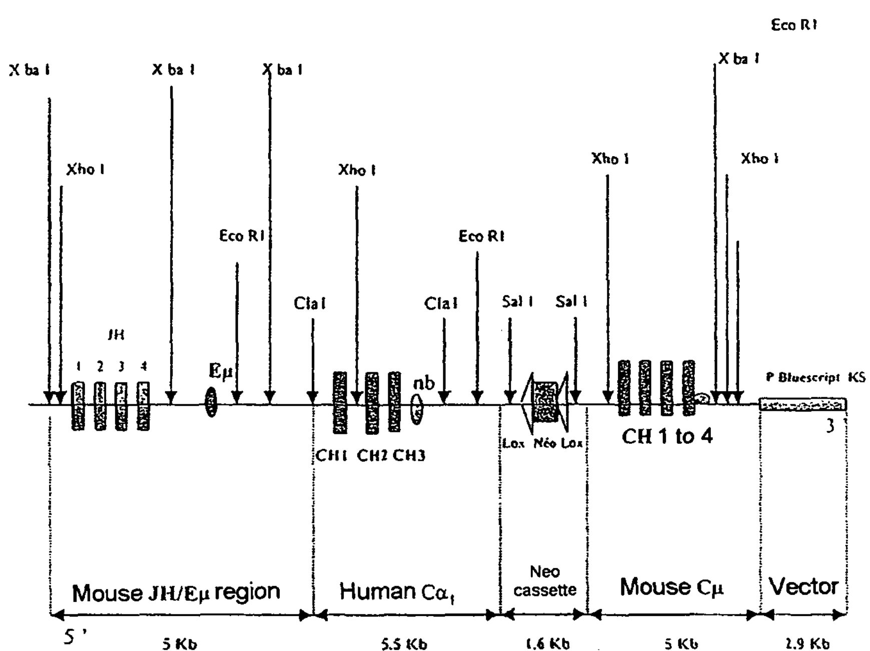

FIG. 2 illustrates the detailed structure of the targeting vector called p-alpha1KI, comprising: a 5.5 kb fragment of the human alpha 1 gene including three exons encoding the constant domains CH1, CH2 and CH3 and the membrane (mb) exon and a neo cassette bordered by LoxP sites (1.6 kb fragment), flanked upstream by a fragment of about 5 kb corresponding to the JH-Eμ region (DQ 52/JH fragment) and downstream by another fragment of about 5 kb corresponding to the Cμ gene (Cμ fragment).

Figure 3:
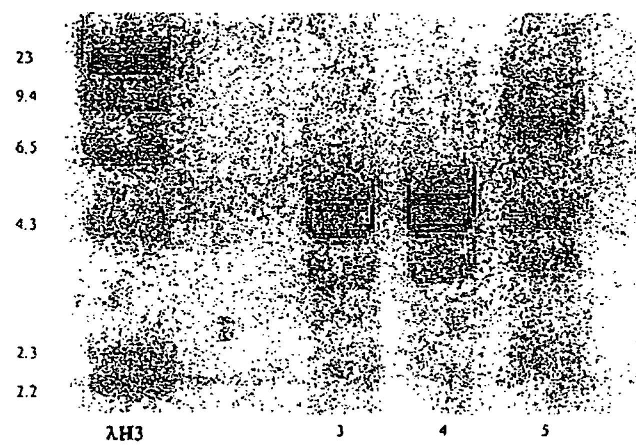

FIG. 3 illustrates the confirmation of the sequence of the targeting vector p-alpha1KI by enzymatic restriction with XhoI. kH3: molecular weight marker. Lanes 3 and 4: clones comprising the neo cassette inserted in the correct orientation; 5 fragments, 2 of which co-migrate (5 kb and 5.3 kb), are detected: 6.4 kb (CH2+CH3 fragment of α1−neo cassette), 5 kb (Cμ fragment), 5.3 kb (JH fragment+CH1 fragment of al) and 3.7 kb (plasmid fragment+5' DQ52 fragment). Lane 5: clone comprising the neo cassette inserted in the reverse orientation; 4 fragments are detected: 9.5 kb (JH fragment−CH2+CH3 fragment of α1−neo cassette), 5 kb (Cμ fragment), 3.7 kb (plasmid fragment+5' DQ52 fragment) and 2.4 kb (CH1 fragment of α1+neo cassette).

Figure 4:
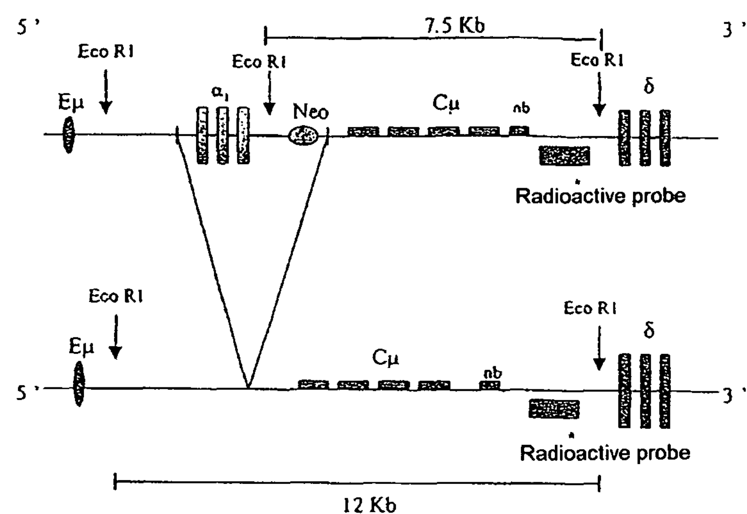

FIG. 4 illustrates the Southern-blot profile of a recombinant allele, compared with a wild-type allele; the genomic DNA digested with EcoRI is hybridized with a probe located in 5' of the δ gene.

Figure 5:
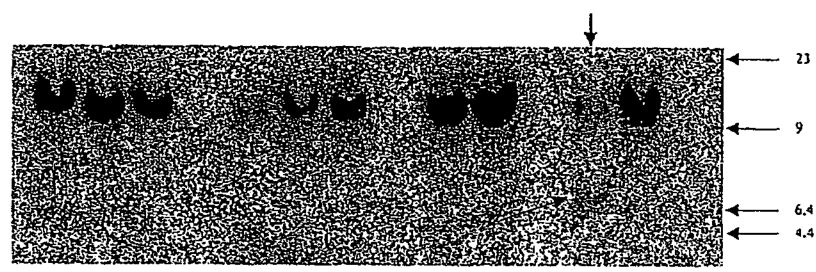

FIG. 5 illustrates the Southern-blot analysis of the genomic DNA of the ES clones transfected with the targeting vector p-alpha1KI; the genomic DNA digested with EcoRI is hybridized with a probe corresponding to the 5' region of the δ gene. The arrow indicates a clone which has integrated the human al transgene by homologous recombination (7.5 kb fragment corresponding to the recombinant allele and 12 kb fragment corresponding to the wild-type allele).

Figure 6:
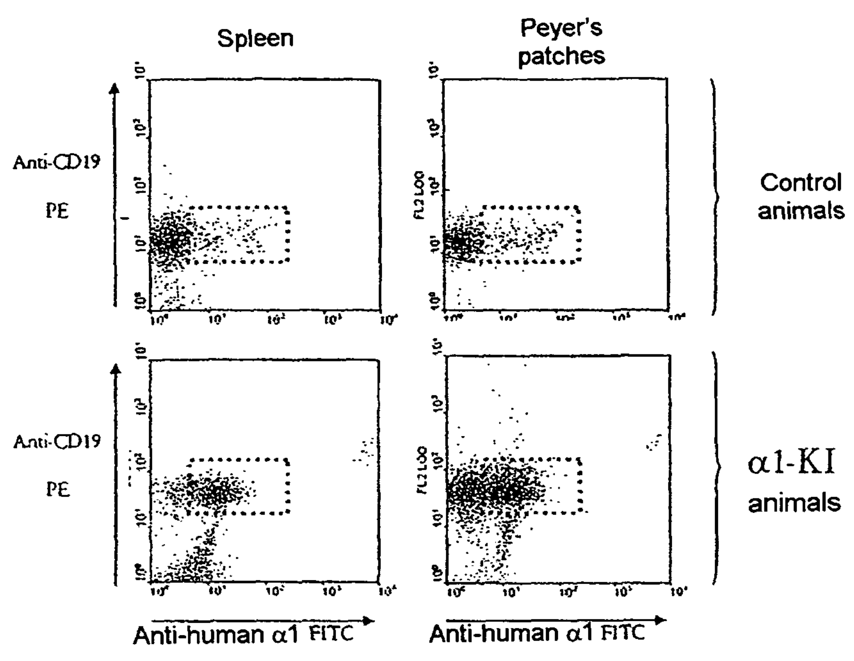

FIG. 6 illustrates the flow cytometry analysis of the expression of a membrane receptor for the human IgA class at the surface of the peripheral lymphocytes of homozygous animals of the transgenic line alpha1KI. The x-axis represents the labeling with an anti-human α1 antibody labeled with fluorescein and the y-axis represents the labeling with an anti-murine CD19 antibody labeled with phycoerythrin. The dotted rectangle indicates the cells expressing both CD19 (B cells) and a human α1 heavy chain.

Figure 7:
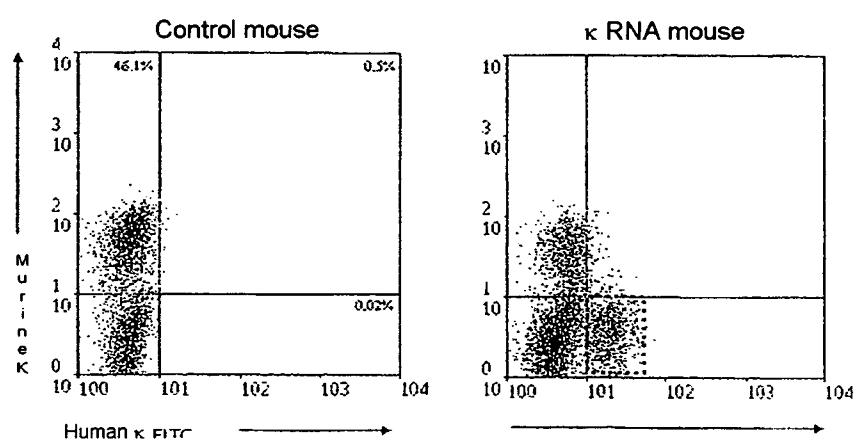

FIG. 7 illustrates the flow cytometry analysis of the expression of the human kappa light chain at the surface of the peripheral B lymphocytes of mice of the kappa RNA line, compared with nontransgenic mice (control). The x-axis represents the labeling with the x-axis represents the labeling with an anti-human kappa antibody labeled with fluorescein and the y-axis represents the labeling with an anti-murine kappa antibody labeled with phycoerythrin.

Figure 8:
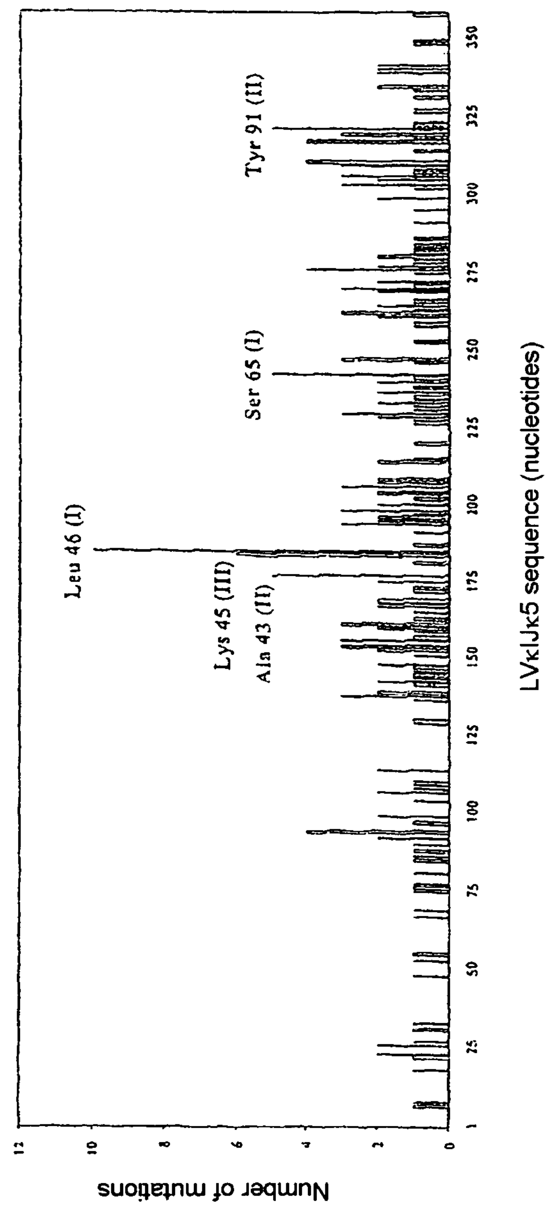

FIG. 8 illustrates the somatic hypermutation of the human kappa transgene in the transgenic mouse line κRNA; the distribution of the mutations along the human kappa light chain of 40 clones isolated from B cells activated with PNA was analyzed. The mutations generating an amino acid substitution, the silent mutations and the mutations generating a stop codon are indicated by ■, □, and ▨ respectively. The amino acids corresponding to the sites of hypermutation are indicated by their nature and their position, and by the position of the mutation in the codon (as a Roman numeral, in parentheses).

Figure 9:
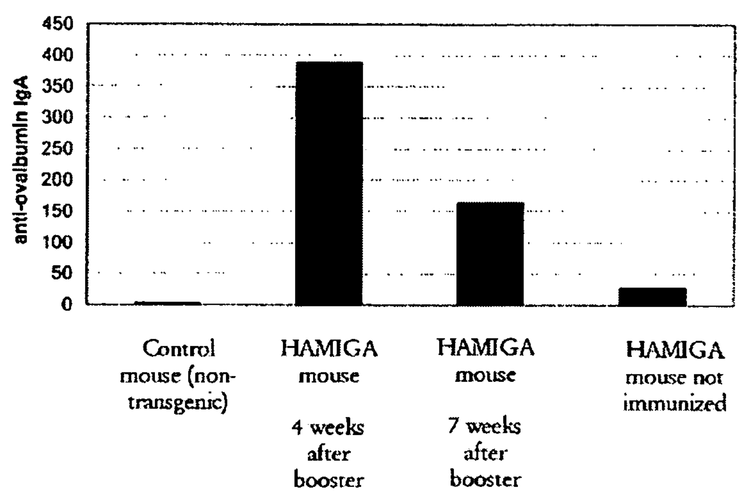

FIG. 9 illustrates the ELISA analysis of the specific human chimeric IgA1 antibody response in the double-transgenic mice of the HAMIGA line immunized with the ovalbumin antigen. The results are expressed as arbitrary units of anti-ovalbumin IgA.

EXAMPLE 1

Production and Characterization of the Transgenic Line Alpha1KI (Alpha1 Knock-In) Expressing a Chimeric Human Immunoglobulin Alpha 1 Heavy Chain The human alpha 1 gene, including the three exons encoding the constant domains CH1, CH2 and CH3 and the membrane (mb) exon, was inserted by homologous recombination, in place of the switch region Sμ of the murine heavy chain (Sμ), so as to block the class switch to the constant genes for immunoglobulins located downstream of Cμ on the endogenous locus (murine IgH locus, FIG. 1). The targeted region abolishes the expression of the endogenous μ gene responsible for the synthesis of IgM heavy chains, and greatly reduces that of other genes for immunoglobulin heavy chains. Consequently, the transgenic line obtained produces a large quantity of chimeric IgAs in which the humanized constant domain corresponds to the IgA1 isotype.

1) Construction of the Homologous Recombination Targeting Vector

The plasmid constructs were produced from the plasmid bluescript SK (pSK) (STRATAGENE) and from the bacterial strain *E.coli* TG1(STRATAGENE), using the conventional protocols for the preparation, cloning and analysis of DNA such as those described in Current Protocols in Molecular Biology (Frederick M. AUSUBEL, 2000, Wiley and Son Inc, Library of Congress, USA).

The homologous recombination vector or targeting vector derived from pSK, called p-alpha1KI (FIG. 2), comprises: a 5.5 kb fragment of the human alpha 1 gene including three exons encoding the constant domains CH1, CH2 and CH3 and the membrane (mb) exon and a neo cassette (1.6 kb fragment), flanked upstream by a fragment of about 5 kb corresponding to the JH-Eμ region (DQ 52/JH fragment) and downstream by another fragment of about 5 kb corresponding to the Cμ gene (Cμ fragment).

More specifically, the various fragments were inserted into the plasmid bluescript SK, according to the following steps:

In a first step, the Cμ fragment corresponding to positions 140101 to 145032 of murine chromosome 12 (Genbank/EMBL AC073553) was amplified by PCR with the aid of appropriate specific primers and then cloned at the XhoI site of pSK to give the plasmid pA.

In a second step, the DQ 52/JH fragment corresponding to positions 131281 to 136441 of murine chromosome 12 (Genbank/EMBL AC073553) was amplified by PCR with the aid of appropriate specific primers and then cloned in 5' of the Cμ fragment, between the EcoRV and ClaI sites of the plasmid pA, to give the plasmid pB.

In a third step, the neo cassette described in Pinaud et al., Immunity, 2001, 15, 187-199 was inserted at the SalI site between DQ52/JH and Cμ, to give the plasmid pC.

The SacI-BamHI fragment of 5.5 kb of a recombinant plasmid comprising the entire human alpha 1 gene, including the exon sequences CH1, CH2 and CH3 (Genbank/EMBL J00220) and the membrane exon (Genbank/EMBL X64133) was ligated at each of its ends with ClaI adaptors.

Finally, in a final step, the 5.5 kb fragment flanked with ClaI adaptors thus obtained was inserted between the JH fragment and the neo cassette at the ClaI site of the plasmid pC to give the targeting vector called p-alpha1KI.

The p-alpha1KI sequence was verified by automated sequencing and by restriction analysis with the enzymes ClaI and XhoI (FIG. 3).

2) Transfection of ES Cells and Injection Into Blastocysts

The clones of ES cells derived from the 129/SJ line were isolated, analyzed and then injected into blastocysts of C57/Black 6 mice using conventional protocols for transgenesis and analysis of genomic DNA, such as those described in Current Protocols in Molecular Biology (Frederick M. AUSUBEL, 2000, Wiley and Son Inc, Library of Congress, USA).

More specifically, ES cells were transfected by electroporation of the p-alpha1KI DNA linearized at the NotI site. The clones selected in the presence of geneticin were collected and the genomic DNA digested with EcoRI was analyzed by Southern blotting with the aid of a radioactive probe hybridizing outside the site of homologous recombination, in 5' of the constant Delta (δ) gene and of its EcoRI site (FIG. 4); this probe, amplified by PCR with the aid of appropriate specific primers, corresponds to positions 140101 to 145032 of the murine chromosome 12 sequence (EMBL/Genbank AC073553).

The presence of a recombinant allele is visualized with a fragment of about 7.5 kb (representing the murine μ fragment and the neo cassette) whereas the wild-type allele corresponds to a fragment of 12 kb (FIG. 5). Under these conditions, out of 303 clones analyzed, 4 proved positive.

Verification of the karyotype of two of the four recombinant clones showed no chromosomal abnormality (aneuploidy).

These clones were injected into blastocysts of C57/Black 6 mice using conventional transgenesis protocols such as those described in *Transgenic Mouse: Methods and Protocols*, cited above. Among the mice obtained, those exhibiting the highest degree of chimerism were analyzed by PCR and by ELISA. A mouse line homozygous for the recombinant IgH locus, called hereinafter alpha 1 knock-in or alpha1KI line, was then obtained by crossing heterozygous animals exhibiting the highest degree of chimerism.

3) Detection of the Recombinant IgH Locus Carrying the Human Cα1 Gene (Alpha 1 Knock-in or Alpha1KI Allele) and of the Wild-type IgH Locus (Wild-type μ Allele) By PCR The genomic DNA of a tail sample from homozygous animals obtained as specified above was analyzed by PCR with the aid of the following two pairs of primers:

pair specific for the non-mutated murine IgH locus (wild-type μ allele):

```
UpstreamSpe I Smu primer:
                                        (SEQ ID NO: 1)
5' GAG TAC CGT TGT CTG GGT CAC 3'

SacI-3' Imu primer:
                                        (SEQ ID NO: 2)
5' GAG CTC TAT GAT TAT TGG TTA AC 3'
```

The amplification reaction was carried out with a hybridization temperature of 61° C. This PCR amplifies in 30 cycles a fragment of 91 base pairs delimiting the SpeI site specific for the nonmutated murine IgH locus.

pair specific for the recombinant IgH locus carrying the human Cα1 gene (alpha 1 knock-in or alpha1KI allele):

```
NeoI primer:
                                        (SEQ ID NO: 3)
5' GCA TGA TCT GGA CGA AGA GCA T 3'

Neo2 primer:
                                        (SEQ ID NO: 4)
5' TCC CCT CAG AAG AAC TCG TCA A 3'
```

The amplification reaction was carried out with a hybridization temperature of 55° C. This PCR amplifies in 30 cycles a fragment of 120 base pairs specific for the recombinant IgH locus carrying the human Cα1 gene (alpha 1 knock-in or alpha1KI mutation).

A mouse line homozygous for the alpha1KI mutation, called hereinafter alpha 1 knock-in or alpha1KI line, was established; the animals of this line are systematically and simultaneously negative in PCR with the primers specific for the wild-type μ allele and positive in PCR with the primers specific for the alpha 1 knock-in allele.

4) Assay of Total Serum IgAs By Nephelometry and By ELISA a) Nephelometry

The serum IgAs were assayed by nephelometry on an automated mchine BNII™ (BEHRING) using the IgA assay kit (BEHRING), according to the supplier's recommendations.

The assay of the serum IgAs gave results which correlated fully with those of the genotyping carried out by PCR:

the non-mutant control animals have a zero level of human class IgA immunoglobulins the heterozygous animals α1-KI also have an undetectable level of human IgAs and a normal level of murine IgMs the homozygous animals α1-KI have a significant level of human IgAs, this level varying between 0.4 and 0.6 g/l in the serum. On the other hand, the murine IgMs are undetectable in the serum of these animals.

b) ELISA

The results obtained by nephelometry were confirmed by ELISA according to the following steps: 96-well plates (Maxisorb™, NUNC) were coated either with non-labeled anti-human IgA antibodies or with non-labeled anti-murine IgM antibodies by incubating overnight at +4° C. in the presence of goat Fab'2 anti-human IgAs or anti-murine IgMs (Southern Biotechnologies Associates), diluted 1/500 in 0.1 M carbonate buffer, pH 8.3 (100 microliters/well). After 3 washings with PBS buffer containing 0.1% Tween (PBS-Tween 0.1%), the plates were saturated in the presence of PBS containing 10% fetal calf serum (100 microliters/well). After 3 washings with PBS-Tween 0.1% buffer, the sera to be tested, diluted 1/100 and 1/500 in PBS buffer containing 10% fetal calf serum were added (100 microliters/well) and the plates were incubated for 3 hours at 37° C. After 3 washings with PBS-Tween 0.1% buffer, an anti-human IgA antiserum labeled with alkaline phosphatase or an anti-murine IgM serum labeled with alkaline phosphatase (Biosys) diluted 1/1000 in PBS-Tween 0.1% (100 microliters/well) were added and the plates were incubated for 1 hour at 37° C. After 3 washings with PBS-Tween 0.1% buffer, the bound IgAs and IgMs were visualized by adding alkaline phosphatase substrate (p-nitrophenyl phosphate, SIGMA) at 1 mg/ml in 0.2M Tris buffer, pH 7.0. The reaction was blocked by adding 0.5N sodium hydroxide (50 microliters/well) and then the absorption was measured at a wavelength of 405 nm.

The quantitative data are obtained by extrapolation with a series for a standard serum (BEHRING) for the assay of the human IgAs, and for a murine monoclonal IgM (SOUTHERN BIOTECHNOLOGIES ASSOCIATES) for the assay of the murine IgMs.

The assay of the serum IgAs by ELISA shows a significant difference between the homozygotes and the heterozygotes; the sera of homozygotes contain 0.4 and 0.6 g/l of IgA1, whereas zero or very low absorbance values are observed for the sera of heterozygotes even at the lowest dilution (1/100). By contrast, when the murine IgMs are assayed by ELISA, a normal murine IgM level is observed (of the order of 1 g/l) in the "non-mutant" control mice and in the animals heterozygous for the α1-KI mutation. On the other hand, the murine IgM level is zero in the animals homozygous for the α1-KI mutation.

5) Investigation of the Expression of a Membrane Receptor for the Human IgA Class at the Surface of the Peripheral Lymphocytes of Mutant Animals The homozygous animals carrying the α1-KI mutation were phenotyped by flow cytometry, by double labeling with the aid of antibodies specific for human IgA1 or murine IgM labeled with fluorescein, and of antibodies specific for B cells (anti-CD19 antibodies) labeled with phycoerythrin. More specifically:

Preparation of lymphoid cells: two peripheral lymphoid organs: the spleen and the Peyer's patches, were removed separately from homozygous mutant animals α1KI, dilacerated in a versene buffer (Invitrogen), and filtered on sieve (40 microns) in order to obtain a suspension of individual cells freed of cellular aggregates. The spleen cells were then centrifuged and subjected to an additional step of osmotic shock in order to lyse the red blood cells by resuspending the cellular pellet in 1 ml of distilled water. The cells of the samples were then immediately resuspended in complete medium (RPMI+10% fetal calf serum), counted and stored on ice.

Labeling with the aid of fluorescent antibodies: $10^5$ cells from each sample were incubated for 30 minutes at 4° C. with a 1/100 dilution, either of an anti-mouse IgM antibody labeled with fluorescein isothiocyanate (Southern Biotechnologies), or of an anti-human IgA antibody labeled with fluorescein isothiocyanate, or alternatively the combination of one of the preceding antibodies with an antibody specific for B cells (anti-CD19 antibodies) labeled with phycoerythrin (double labeling). The cells were then washed in 5 ml of PBS and then the supernatant was separated after decantation and the cells were resuspended in 100 microliters of PBS, 0.5% BSA, 0.1 mM EDTA.

Cytofluorimetric analysis: the labeled cells were analyzed by flow cytometry (COULTER XL™).

The results of the flow cytometry are in agreement with those of the assay of serum immunoglobulins. In the homozygous animals of the alpha1-KI line, no expression of murine IgMs is detected either in the spleen or in the Peyer's patches.

Yet in the absence of expression of IgM, a compartment of CD19+ peripheral B cells is capable of becoming differentiated in these animals and represents 10 to 12% of the spleen lymphocytes or 40 to 60% of the lymphocytes of the Peyer's patches. This compartment expresses membrane IgAs in which the humanized heavy chain is recognized by an antibody specific for the IgA1s and labeled with fluoroscein (FIG. 6).

EXAMPLE 2

Production and Characterization of the Transgenic Line κ RNA Expressing a Human Immunoglobulin Kappa Light Chain A transgenic animal line expressing in all their B cells a human kappa light chain encoded by the variable region VκI-Jκ5 and the Cκ region (kappa RNA chain, EMBL/Genbank X64133) was obtained by direct transgenesis from the expression vector described in Chauveau et al., Gene, 1998, 222, 279-285.

1) Construction of the Transgenesis Vector

The transgenesis vector is the plasmid pALIEμ described in Chauveau et al., Gene, 1998, 222, 279-285; it contains both the VH promoter and the Eμ enhancer in 5' of the cassette encoding the kappa RNA chain, and in 3' of this cassette: the three enhancers hs3a, hs12 and hs3b, located in 3' of the IgH locus in 3'. The coding sequence corresponds to the VκI-Jκ5-Cκ chain (Genbank/EMBL X64133). The plasmid pALIEμ was linearized with the restriction enzymes NotI and PvuI which cut inside the plasmid sequence, NotI being located upstream of the promoter which precedes the cloned Vκ segment and PvuI being located within the ampicillin resistance gene carried by the plasmid. The fragment including the entire kappa expression cassette flanked by all the promoter and regulatory elements for expression was then randomly inserted into mouse blastocysts using conventional direct transgenesis protocols such as those described in *Transgenic Mouse: Methods and Protocols*, cited above.

2) Identification of the Founder Animals of the κ RNA Line and Typing of Their Progeny A transgenic mouse line possessing the κ RNA transgene was obtained after injection of the expression vector; the presence of this human transgene was verified on the DNA of the mice by Southern blotting with the aid of a probe specific for the human Cκ region (EcoRI-EcoRI fragment of 2.5 kb including the entire human Cκ exon). The animals carrying the insert of the transgene on the two alleles of the site of insertion (homozygous animals) have a double quantity of transgene and can be distinguished by Southern blotting from the animals carrying a single copy of the transgene (heterozygous animals). Alternatively, the presence of the transgene was detected by PCR with the aid of primers which make it possible to specifically amplify the human sequence VκI-Jκ5-Cκ (Genbank/EMBL X64133).

3) Investigation of the Expression of the Human Kappa Light Chains at the Surface of the Peripheral Lymphocytes of Mice of the Kappa RNA Line The dizygous animals carrying the kappa RNA transgene were phenotyped by flow cytometry, by double labeling with the aid of an anti-murine κ antibody (labeled with phycoerythrin) in conjunction with an anti-human κ antibody (labeled with fluorescein isothiocyanate), according to the protocol as described in example 1.

These animals show an expression of the human κ transgene on the majority of the B cells (FIG. 7). Furthermore, the transgene induces a phenomenon of allelic exclusion such that the B cells expressing the human κ transgene do not express an endogenous gene for the mouse light chains. By cytometry, these cells are therefore positive during labeling with the anti-human κ chain antiserum and negative with the anti-murine κ chain antiserum (FIG. 7).

4) Analysis of the Somatic Hypermutation of the κ Transgene in Mice of the Kappa RNA Line It has been shown that this human κ light chain is capable of combining with heavy chains and of becoming diversified by virtue of the phenomenon of somatic hypermutation (triggered by a response to the antigen). This transgene which preserves the endogenous architecture of a κ gene with presence of the Jκ-Cκ intron between VκJκ and Cκ, further benefits from a high expression provided by the $P_{VH}$ promoter/Eμ enhancer+regulatory palindrome 3'IgH (hs3a, hs1,2, hs3b) combination. The cumulative action of all these regulatory elements makes it possible to recruit the somatic hypermutation machinery at the level of the transgene. More specifically, the Peyer's patches of transgenic mice are removed by dissection of the intestine. The cellular suspension is prepared by grinding the Peyer's patches through a nylon membrane. The cells are washed three times at +4° C. in DMEM containing 10% fetal calf serum. The dead cells were removed after each washing and the cellular suspension was adjusted to $10^6$ cells/ml.

The cells were incubated for 30 min at +4° C. in the presence of biotinylated anti-B220 antibodies. After two washings with DMEM containing 5% fetal calf serum, the cells were incubated for 30 min at +4° C. in the presence of streptavidin coupled to phycoerythrin, and then washed and resuspended in PBS containing 5% fetal calf serum. After adding a lectin specific for the activated B cells (PNA for peanut agglutinin) conjugated with FITC, the cellular suspension was incubated for 30 min at +4° C. After two washings with DMEM, the cells were resuspended in DMEM and then they were sorted, by flow cytometry, into two populations: $B220^+$ $PNA^{high}$ (activated B) and $B220^+PNA^{low}$ (resting B).

The genomic DNA was extracted from the two cellular populations sorted with the aid of the kit QIAamp Tissue (QIAGEN). Amplification by polymerase chain reaction (PCR) was carried out on 2 μl of genomic DNA using primers corresponding to the signal region of the human Vκ1 (5'-AAGTCGACATGGACATGAGGGTGCC-3') (SEQ ID NO:5) and at the beginning of the human Jκ5 region (5'-TTCTCGAGACTTAGGTTTAATCTCCAG-3') (SEQ ID NO:6). The amplification program consisted of: an initial step of denaturation at 94° C. for 5 min; followed by 35 cycles consisting of a denaturation step at 94° C. for 30 s, a hybridization step at 52° C. for 30 s and an extension step at 72° C. for 30 s; and then a final extension step at 72° C. for 7 min.

The amplification product was purified on 1.2% agarose gel, eluted (kitQIAquick Gel Extraction kit, QUIAGEN) and then cloned into the vector pCRII-TOPO (INVITROGEN). The recombinant clones were tested by enzyme restriction and then purified (Flexiprep kit, PHARMACIA) and sequenced by the Sanger method. The sequencing reactions were carried out by PCR with the aid of the primers M13 reverse and M13(−20) and fluorescent dideoxynucleotides and then analyzed by capillary electrophoresis on an automated sequencer (ABI-PRISM 310, PERKIN-ELMER). The sequences obtained from the activated B cells were then aligned with the original sequence of the non-mutated transgene (Genbank/EMBL X64133). The number and the position of the mutations were analyzed (FIG. 8).

The κ transgene undergoes this somatic hypermutation at a rate which is practically as high (17 mutations per 1000 bases) as the endogenous immunoglobulin genes (which mutate at a rate of 40 mutations per 1000 bases). This single transgene is therefore capable of generating a kappa "repertoire" having some diversity.

EXAMPLE 3

Production and Characterization of the Double-transgenic HAMIGA Line Expressing a Chimeric Alpha 1 Heavy Chain and a Kappa Light Chain of Human Immunoglobulins The crossing of the KRNA and alpha1-KI lines described in the preceding examples generates double transgenic KRNA/alpha1-KI mice.

To do this, the animals homozygous for the alpha1-KI mutation and homozygous for the κ RNA transgene were crossed with each other. In the first generation (F1) after this crossing, all the animals obtained are heterozygous for the alpha1-KI mutation and heterozygous for the κ RNA transgene. These F1 animals were therefore crossed again: in the next generation (F2) the laws of Mendelian genetics make it possible to obtain 1 animal out of 4 homozygous for the alpha1-KI mutation and one animal out of 4 homozygous for the κ RNA transgene. Among these F2 animals, one animal out of 16 could therefore be selected as carrying both the alpha1-KI mutation in the homozygous state and carrying the κ RNA transgene in the homozygous state. These animals are the founders of the HAMIGA line and they stably transmit to their progeny the genes which simultaneously allow the production of a humanized alphal heavy chain in place of the production of murine IgMs and the production and diversification by hypermutation of a human κ chain.

This double transgenic mouse line is called HAMIGA line for "Humanized Antibodies Made Up Of Monoclonal Immunoglobulin A".

1) Production of the Double-transgenic HAMIGA Line a) Presence of the κ Transgene The transmission of the κ RNA transgene during crossings of transgenic animals was monitored by Southern blotting with the aid of a probe specific for the human Cκ region (EcoRI-EcoRI fragment of 2.5 kb including the entire human Cκ exon).

The expression of the κ transgene in the mutant animals was detected by ELISA assay of free human kappa chains eliminated in the urine of the animal. More specifically: 96-well plates (Maxisorb®, NUNC) were incubated overnight at +4° C. in the presence of a non-labeled anti-human κ antibody (Kallestad) diluted 1/1000 in 0.1M carbonate buffer pH 8.3 (100 microliters/well). After 3 washings with PBS buffer containing 0.1% Tween (PBS-Tween 0.1%), the plates were saturated in the presence of PBS containing 10% fetal calf serum (100 microliters/well). After 3 washings with PBS-Tween 0.1% buffer, the urine samples to be tested, diluted 1/100 and 1/500 in PBS buffer containing 10% fetal calf serum were added (100 microliters/well) and the plates were incubated for 3 hours at 37° C. After 3 washings with PBS-Tween 0.1% buffer, an anti-human κ antiserum labeled with alkaline phosphatase (SIGMA) diluted 1/1000 in PBS-Tween 0.1% (100 microliters/well) was added and the plates were incubated for 1 hour and at 37° C. After 3 washings with PBS-Tween 0.1% buffer, the bound human kappa light chains were visualized by adding alkaline phosphatase substrate (p-nitrophenyl phosphate, SIGMA) at 1 mg/ml in 0.2 M Tris buffer, pH 7.0. The reaction was blocked by adding 0.5N sodium hydroxide (50 microliters/well) and then the absorption was measured at a wavelength of 405 nm.

Alternatively, the expression of the human kappa transgene was analyzed by flow cytometry as described in example 2. The results show that the presence of the κ RNA transgene causes an important phenomenon of allelic exclusion, such that among the peripheral lymphocytes more than 50% express the human light chain and do not therefore rearrange the genes for the murine light chains in order to express a murine light chain.

b) Homozygosity for the α1-KI Mutation

The first single element indicating α1-KI homozygocity is the presence of a high level of human IgA1s in the serum of the animals. In addition, the homozygocity was confirmed by PCR by the positivity of the "α1-KI PCR" combined with the negativity of the "wild-type μ allele PCR". Finally, after sacrificing the animals, flow cytometry analysis made it possible to show on the lymphocytes of the spleen and of the Peyer's patches that the entire B lymphocytes (CD19+) express membrane human IgA1s whereas in parallel no B cell expresses murine IgM.

c) Verification of the Simultaneous Presence of the Alpha1-KI Mutation and of the κ RNA Transgene in the HAMIGA Animals and Their Progeny The double-transgenic HAMIGA animals were characterized as those simultaneously corresponding to the two specificities described above: the presence of the K RNA transgene in the homozygous state and the homozygocity for the alpha1-KI mutation. Furthermore, these animals reproduce while preserving these two specificities and the phenotype of their progeny has the following properties, simultaneously and in a stable manner:

- the production of humanized IgA1 at a sizable level (easily verifiable by ELISA or nephelometry on a simple blood sample taken from live animals at the level of the retro-orbital sinus)
- the production of human κ light chain (easily verifiable by ELISA on a simple urine sample taken from live animals).

2) Immunization of the Animals

The animals were immunized once by intraperitoneal injection of 10 micrograms of ovalbumin (SIGMA) diluted in 100 microliters of physiological saline and emulsified with 200 microliters of Freund's complete adjuvant (SIGMA).

After 4 weeks, the animals were subjected to a vaccine booster by intraperitoneal injection of 10 micrograms of ovalbumin (SIGMA) diluted in 100 microliters of physiological saline and emulsified with 200 microliters of Freund's incomplete adjuvant (SIGMA).

3) Assay of the Antibodies Specific for the Vaccine Antigen (Ovalbumin)

The presence of antibodies specific for the vaccine antigen ovalbumin was analyzed by ELISA 4 weeks, and then 7 weeks after the second injection of the antigen, according to the following technique: 96 well-plates (Maxisorb®, NUNC) were incubated overnight at +4° C. in the presence of ovalbumin at the concentration of 10 micrograms/ml in 0.1M carbonate buffer pH 8.3 (100 microliters/well). After 3 washings with PBS buffer containing 0.1% Tween (PBS-Tween 0.1%) the plates were saturated in the presence of PBS containing 10% fetal calf serum (100 microliters/well). After 3 washings with PBS-Tween 0.1% buffer, the serum samples to be tested, diluted 1/20 and 1/100 in PBS buffer containing 10% fetal calf serum were added (100 microliters/well) and the plates were incubated for 3 hours at 37° C. After 3 washings with PBS-Tween 0.1% buffer, an anti-human IgA antiserum labelled with alkaline phosphatase (BIOSYS) diluted 1/1000 in PBS/Tween 0.1% (100 microliters/well) was added and the plates were incubated for 1 hour at 37° C. After 3 washings with PBS-Tween 0.1% buffer, the bound human kappa light chains were visualized by adding alkaline phosphatase substrate (p-nitrophenyl phosphate, SIGMA) at 1 mg/ml in 0.2M Tris buffer, pH 7.0. The reaction was blocked by adding 0.5N sodium hydroxide (50 microliters/well) and then the absorption was measured at a wavelength of 405 nm. The level of anti-ovalbumin IgA antibodies was expressed as arbitrary units established for sera diluted 1/100 as a function of the Optical density tested serum/Optical density control serum ratio.

The results presented in FIG. 9 show the presence of antibodies specific for the vaccine antigen ovalbumin 4 weeks (level of human anti-ovalbumin IgA1 antibodies at 388 units), and then 7 weeks after the second injection of the antigen (level of anti-ovalbumin IgA antibodies at 162 units). In parallel, it was also verified that in the absence of immunization of the animals, the level of the anti-ovalbumin IgA antibodies detected remained less than 30 units.

The repertoire of response to the antigens of these mice is expected as subnormal since it is known that it is essentially the VH domain of the heavy chain which contributes to the formation of the antibody site (yet the human transgenic al heavy chain benefits from a completely diversified repertoire since it corresponds to the normal repertoire generated by the rearrangements of the VH, D and JH segments of the murine IgH locus). These mice are capable of producing antibodies of high affinity as a secondary response, which results from the fact that their B lymphocytes can recruit the phenomenon of somatic hypermutation both at the level of the heavy chain gene and of the κ RNA light chain transgene.

As is evident from the above, the invention is not at all limited to its embodiments, implementations and applications which have just been described more explicitly; it embraces on the contrary all the variants which may occur to the specialist in this field, without departing from the framework or the scope of the present invention.

The invention claimed is:

1. A transgenic mouse, wherein an endogenous IgH locus comprises replacement of its switch sequence Sμ with a transgene consisting essentially of a human class A immunoglobulin heavy chain constant region gene Cα or a segment of said Cα gene comprising at least an exon encoding the CH3 domain and a membrane exon, wherein said transgenic mouse produces chimeric immunoglobulins A whose heavy chains comprise a mouse variable region and a human constant region or a segment thereof comprising at least the CH3 domain, and wherein said transgenic mouse produces no mouse immunoglobulins M.

2. The transgenic mouse of claim 1, which is homozygous for said modified IgH locus.

3. The transgenic mouse of claim 1, wherein said transgene consists of the entire Cα gene.

4. The transgenic mouse of claim 1, wherein said transgene consists of the segment of the Cα gene comprising the exon encoding the CH3 domain and the membrane exon.

5. The transgenic mouse of claim 1, wherein said Cα gene is the Cα1 gene.

6. The transgenic mouse of claim 1, which further comprises another transgene encoding a human immunoglobulin light chain.

7. The transgenic mouse of claim 6, wherein said light chain is a kappa light chain.

8. The transgenic mouse of claim 6, wherein said transgene which encodes a human immunoglobulin kappa light chain, further comprises the intronic activator Eμ upstream of a DNA sequence encoding said human immunoglobulin kappa light chain and the palindrome hs3a/hs1,2/hs3b downstream of said DNA sequence.

9. The transgenic mouse of claim 8, wherein said transgene is under the control of the promoter of the human immunoglobulin heavy chain.

10. The transgenic mouse of claim 6, which is dizygous for said transgene.

11. The transgenic mouse of claim 6, further comprising an inactivated endogenous immunoglobulin kappa light chain locus.

12. The transgenic mouse of claim 11, which is homozygous for said inactivated endogenous immunoglobulin kappa light chain locus.

13. The transgenic mouse of claim 1, further comprising an inactivated endogenous J chain gene.

14. The transgenic mouse of claim 13, which is homozygous for said inactivated endogenous J chain gene.

15. The transgenic mouse of claim 13, which further comprises another transgene encoding a human immunoglobulin J chain gene.

16. The transgenic mouse of claim 1, wherein said:

a) endogenous mouse IgH locus comprises the replacement of its switch sequence Sμ with the entire human class A immunoglobulin heavy chain constant region gene Cα1, and b) which transgenic mouse further comprises a human kappa light chain transgene comprising a VκI gene rearranged with a Jκ5 gene, a Jκ-Cκ intron and a Cκ gene, under the transcriptional control of the human heavy chain promoter (pVH), the intronic activator Eμ upstream of said promoter of and the palindrome hs3a/hs1,2/hs3b downstream of said Cκ gene.

17. A homologous recombination targeting vector, which comprises a human class A immunoglobulin heavy chain constant region gene Cα or a segment of said Cα gene comprising at least an exon encoding the CH3 domain and a membrane exon, flanked by the sequences SEQ ID NO: 7 and SEQ ID NO: 8.

18. The targeting vector of claim 17, which comprises a cassette for expressing a selection marker, adjacent to said Cα gene or to a segment of said gene.

19. The targeting vector of claim 18, wherein said expression cassette is flanked by site-specific recombination sequences.

20. The targeting vector of claim 19 wherein said sequences are LoxP sequences of Cre recombinase.

21. A mouse embryonic cell, which is modified with the targeting vector of claim 17.

22. A method for preparing humanized class IgA antibodies or fragments thereof, which comprises at least the following steps:

a) immunizing the transgenic mouse of claim 1, and b) producing humanized class IgA antibodies or fragments of the antibodies from serum secretions or B lymphocytes of said transgenic mouse sacrificed beforehand.

* * * * *

```
                          SEQUENCE LISTING


<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1

gagtaccgtt gtctgggtca c                                              21


<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2

gagctctatg attattggtt aac                                            23


<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3

gcatgatctg gacgaagagc at                                             22


<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4

tcccctcaga agaactcgtc aa                                             22


<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5

aagtcgacat ggacatgagg gtgcc                                          25


<210> SEQ ID NO 6
<211> LENGTH: 27
<212> TYPE: DNA
<213> ORGANISM: Artificial Sequence
<220> FEATURE:
```

<223> OTHER INFORMATION: Description of Artificial Sequence: Synthetic primer

<400> SEQUENCE: 6

```
ttctcgagac ttaggtttaa tctccag                                        27
```

<210> SEQ ID NO 7
<211> LENGTH: 5161
<212> TYPE: DNA
<213> ORGANISM: Mus musculus

<400> SEQUENCE: 7

```
acaggcctga gagaacagac tctggaaata gatgggactt acggagctaa gatctagagc     60
tcatctacag agcagaatcc cagccaagag aacaaagaat actgactctc tcctgttccc    120
tactcctaga gttctaaaac acactatagg gaagggagcc tctagacctc cgtccattcc    180
ccatcttgct cattccatct tcccatgtcc ccaggtctcc aagccacaga caccaccttt    240
cctattcacc cacctttctg tgtccctagg tccccaggcc atagtcacct ccccccacac    300
cccgctcacc ctgccccatc tatgccccta gatgcttact taccagagtc ttttgtctga    360
cgtggggcta caagcatcta tgctccctaa gcacctactg ctgacctgta ggacccagct    420
ctgaaccaac tcatataagt aaatacagac tctcccctgt cttaggatgg ccccctgggt    480
caggaggaga ccactgccaa ggaaccttct cttagagcac tgaactcctc ccctgtacca    540
cttaggacag acctgagacc tattattact gattaccaga gctctggcag tgaccacgga    600
ggagatagat ccaccctgga cacaggaaac acagcaccag agatactgct tcatcacaac    660
agtagagtga cactttagac tttaatttgg gtcactttcc tgctgtagag gtgggatcag    720
aaagcaaaga gcagtatgag tgcctgatag gcacccaagt acactataga gtactcatgg    780
tgaataaggt acctccatgg cttcccaggg aggggcactg ccccaccccc accatcacag    840
acctttctcc atagttgata actcagacac aagtgaatga cagatggacc tccatctgct    900
cttattttaa aaagaagaca aaccccacag gctcgagaac tttagcgact gttttgagag    960
aaatcattgg tccctgactc aagagatgac tggcagattg gggatcagaa tacccatact   1020
ctgtggctag tgtgaggttt aagcctcaga gtccctgtgg tctctgactg gtgcaaggtt   1080
ttgactaagc ggagcaccac agtgctaact gggaccacgg tgacacgtgg ctcaacaaaa   1140
accttctgtt tggagctctc caggggcagc ctgagctatg aggaagtaga gaggcttgag   1200
aaatctgagg aagaaaagag tagatctgag aggaaaggta gctttctgga ggtcaggaga   1260
cagtgcagag aagaacgagt tactgtggac aggtcttaga tggggaaaga atgagcaaat   1320
gcaagcatca gaagggtgga tgcaatgtcc tgccaaggac ttaccaagag gatccccgga   1380
cagagcaggc aggtggagtt gactgagagg acaggatagg tgcaggtccc tctcttgttt   1440
cctttctcct tctcctgttt ccttcttctc ttgtcacagg tctcactatg ctagccaagg   1500
ctagcctgaa agattaccat cctacagatg ggcccatcca gttgaattaa ggtggagatc   1560
tctccaaaca tctgagtttc tgaggcttgg atgccactgg ggacgccaag ggactttggg   1620
atgggtttgg ttggccccag atgaagggct acttcactgg gtctataatt actctgatgt   1680
ctaggaccag gggctcagg tcactcaggt caggtgagtc ctgcatctgg ggactgtggg   1740
gttcaggtgg cctaaggcag gatgtggaga gagttttagt ataggaacag aggcagaaca   1800
gagactgtgc tactggtact tcgatgtctg gggcacaggg accacggtca ccgtctcctc   1860
aggtaagctg gctttttttct ttctgcacat tccattctga aacgggaaaa gatattctca   1920
gatctcccca tgtcaggcca tctgccacac tctgcatgct gcagaagctt ttctgtaagg   1980
```

-continued

```
atagggtctt cactcccagg aaaagaggca gtcagaggct agctgcctgt ggaacagtga   2040
caatcatgga aaataggcat ttacattgtt aggctacatg ggtagatggg tttttgtaca   2100
cccactaaag ggtctatga tagtgtgact actttgacta ctggggccaa ggcaccactc   2160
tcacagtctc ctcaggtgag tccttacaac ctctctcttc tattcagctt aaatagattt   2220
tactgcattt gttggggggg aaatgtgtgt atctgaattt caggtcatga aggactaggg   2280
acaccttggg agtcagaaag ggtcattggg agccctggct gacgcagaca gacatcctca   2340
gctcccatac ttcatggcca gagatttata gggatcctgg ccagcattgc cgctaggtcc   2400
ctctcttcta tgctttcttt gtccctcact ggcctccatc tgagatcatc ctggagccct   2460
agccaaggat catttattgt caggggtcta atcattgttg tcacaatgtg cctggtttgc   2520
ttactggggc caagggactc tggtcactgt ctctgcaggt gagtcctaac ttctcccatt   2580
ctaaatgcat gttgggggga ttctgggcct tcaggaccaa gattctctgc aaacgggaat   2640
caagattcaa cccctttgtc ccaaagttga gacatgggtc tgggtcaggg actctctgcc   2700
tgctggtctg tggtgacatt agaactgaag tatgatgaag gatctgccag aactgaagct   2760
tgaagtctga ggcagaatct tgtccagggt ctatcggact cttgtgagaa ttaggggctg   2820
acagttgatg gtgacaattt cagggtcagt gactgtctgg tttctctgag gtgaggctgg   2880
aatataggtc accttgaaga ctaaagaggg gtccaggggc ttctgcacag gcagggaaca   2940
gaatgtggaa caatgacttg aatggttgat tcttgtgtga caccaggaat tggcataatg   3000
tctgagttgc ccaggggtga ttctagtcag actctggggt ttttgtcggg tatagaggaa   3060
aaatccacta ttgtgattac tatgctatgg actactgggg tcaaggaacc tcagtcaccg   3120
tctcctcagg taagaatggc ctctccaggt ctttattttt aacctttgtt atggagtttt   3180
ctgagcattg cagactaatc ttggatattt gtccctgagg gagccggctg agagaagttg   3240
ggaaataaac tgtctaggga tctcagagcc tttaggacag attatctcca catctttgaa   3300
aaactaagaa tctgtgtgat ggtgttggtg gagtccctgg atgatgggat agggactttg   3360
gaggctcatt tgaagaagat gctaaaacaa tcctatggct ggagggatag ttggggctgt   3420
agttggagat tttcagtttt tagaataaaa gtattagttg tggaatatac ttcaggacca   3480
cctctgtgac agcatttata cagtatccga tgcataggga caaagagtgg agtggggcac   3540
tttctttaga tttgtgagga atgttccgca ctagattgtt taaaacttca tttgttggaa   3600
ggagagctgt cttagtgatt gagtcaaggg agaaaggcat ctagcctcgg tctcaaaagg   3660
gtagttgctg tctagagagg tctggtggag cctgcaaaag tccagctttc aaaggaacac   3720
agaagtatgt gtatggaata ttagaagatg ttgcttttac tcttaagttg gttcctagga   3780
aaaatagtta aatactgtga ctttaaaatg tgagagggtt ttcaagtact cattttttta   3840
aatgtccaaa attcttgtca atcagtttga ggtcttgttt gtgtagaact gatattactt   3900
aaagtttaac cgaggaatgg gagtgaggct ctctcataac ctattcagaa ctgactttta   3960
acaataataa attaagtttc aaatattttt aaatgaattg agcaatgttg agttggagtc   4020
aagatggccg atcagaacca gaacacctgc agcagctggc aggaagcagg tcatgtggca   4080
aggctatttg gggaagggaa aataaaacca ctaggtaaac ttgtagctgt ggtttgaaga   4140
agtggttttg aaacactctg tccagcccca ccaaaccgaa agtccaggct gagcaaaaca   4200
ccacctgggt aatttgcatt tctaaaataa gttgaggatt cagccgaaac tggagaggtc   4260
ctcttttaac ttattgagtt caacctttta attttagctt gagtagttct agtttcccca   4320
aacttaagtt tatcgacttc taaaatgtat ttagaattca ttttcaaaat taggttatgt   4380
```

```
aagaaattga aggactttag tgtctttaat ttctaatata tttagaaaac ttcttaaaat   4440
tactctatta ttcttccctc tgattattgg tctccattca attcttttcc aatacccgaa   4500
gcatttacag tgactttgtt catgatcttt tttagttgtt tgttttgcct tactattaag   4560
actttgacat tctggtcaaa acggcttcac aaatcttttt caagaccact ttctgagtat   4620
tcattttagg agaaagactt ttttttaaa tgaatgcaat tatctagact tatttcagtt   4680
gaacatgctg gttggtggtt gagaggacac tcagtcagtc agtgacgtga agggcttcta   4740
agccagtcca catgctctgt gtgaactccc tctggccctg cttattgttg aatgggccaa   4800
aggtctgaga ccaggctgct gctgggtagg cctggacttt gggtctccca cccagacctg   4860
ggaatgtatg gttgtggctt ctgccaccca tccacctggc tgctcatgga ccagccagcc   4920
tcggtggctt tgaaggaaca attccacaca aagactctgg acctctccga aaccaggcac   4980
cgcaaatggt aagccagagg cagccacagc tgtggctgct gctcttaaag cttgtaaact   5040
gtttctgctt aagagggact gagtcttcag tcattgcttt agggggagaa agagacattt   5100
gtgtgtcttt tgagtaccgt tgtctgggtc actcacattt aactttcctt gaaaaactag   5160
t                                                                   5161
```

<210> SEQ ID NO 8
<211> LENGTH: 4932
<212> TYPE: DNA
<213> ORGANISM: Mus musculus

<400> SEQUENCE: 8

```
tagcagggtg tagagggatc tcctgtctga caggaggcaa gaagacagat tcttacccct     60
ccatttctct tttatccctc tctggtcctc agagagtcag tccttcccaa atgtcttccc    120
cctcgtctcc tgcgagagcc ccctgtctga taagaatctg gtggccatgg gctgcctggc    180
ccgggacttc ctgcccagca ccatttcctt cacctggaac taccagaaca acactgaagt    240
catccagggt atcagaacct tcccaacact gaggacaggg ggcaagtacc tagccacctc    300
gcaggtgttg ctgtctccca agagcatcct tgaaggttca gatgaatacc tggtatgcaa    360
aatccactac ggaggcaaaa acaaagatct gcatgtgccc attccaggta agaaccaaac    420
cctcccagca ggggtgccca ggcccaggca tggcccagag ggagcagcgg ggtggggctt    480
aggccaagct gagctcacac cttgaccttt cattccagct gtcgcagaga tgaaccccaa    540
tgtaaatgtg ttcgtcccac cacgggatgg cttctctggc cctgcaccac gcaagtctaa    600
actcatctgc gaggccacga acttcactcc aaaaccgatc acagtatcct ggctaaagga    660
tgggaagctc gtggaatctg gcttcaccac agatccggtg accatcgaga acaaaggatc    720
cacaccccaa acctacaagg tcataagcac acttaccatc tctgaaatcg actggctgaa    780
cctgaatgtg tacacctgcc gtgtggatca caggggtctc accttcttga agaacgtgtc    840
ctccacatgt gctgccagtg agtggcctgg gctaagccca atgcctagcc ctcccagatt    900
agggaagtcc tcctacaatt atggccaatg ccacccagac atggtcattt gctccttgaa    960
ctttggctcc ccagagtggc caaggacaag aatgagcaat aggcagtaga ggggtgagaa   1020
tcagctggaa ggaccagcat cttcccttaa gtaggtttgg gggatggaga ctaagctttt   1080
ttccaacttc acaactagat atgtcataac ctgacacagt gttctcttga ctgcaggtcc   1140
ctccacagac atcctaacct tcaccatccc cccctccttt gccgacatct tcctcagcaa   1200
gtccgctaac ctgacctgtc tggtctcaaa cctggcaacc tatgaaaccc tgaatatctc   1260
ctgggcttct caaagtggtg aaccactgga aaccaaaatt aaaatcatgg aaagccatcc   1320
```

```
caatggcacc ttcagtgcta agggtgtggc tagtgtttgt gtggaagact ggaataacag   1380
gaaggaattt gtgtgtactg tgactcacag ggatctgcct tcaccacaga agaaattcat   1440
ctcaaaaccc aatggtaggt atcccccctt cccttcccct ccaattgcag gacccttcct   1500
gtacctcata gggagggcag gtcctcttcc accctatcct cactactgtc ttcatttaca   1560
gaggtgcaca aacatccacc tgctgtgtac ctgctgccac cagctcgtga gcaactgaac   1620
ctgagggagt cagccacagt cacctgcctg gtgaagggct tctctcctgc agacatcagt   1680
gtgcagtggc ttcagagagg gcaactcttg ccccaagaga agtatgtgac cagtgccccg   1740
atgccagagc ctggggcccc aggcttctac tttacccaca gcatcctgac tgtgacagag   1800
gaggaatgga actccggaga gacctatacc tgtgttgtag gccacgaggc cctgccacac   1860
ctggtgaccg agaggaccgt ggacaagtcc actggtaaac ccacactgta caatgtctcc   1920
ctgatcatgt ctgacacagg cggcacctgc tattgaccat gctagcgctc aaccaggcag   1980
gccctgggtg tccagttgct ctgtgtatgc aaactaacca tgtcagagtg agatgttgca   2040
ttttataaaa attagaaata aaaaaaatcc attcaaacgt cactggtttt gattatacaa   2100
tgctcatgcc tgctgagaca gttgtgtttt gcttgctctg cacacaccct gcatacttgc   2160
ctccaccctg gcccttcctc taccttgcca gtttcctcct tgtgtgtgaa ctcagtcagg   2220
cttacaacag acagagtatg aacatgcgat tcctccagct acttctagat atatggctga   2280
aagcttgcct aacctggtgc aggcagcatt caggcacata tatagacaca catgcattta   2340
tacatagata tataggtaca catgtgtaga cacatacatg aatgtgtatt catggacaca   2400
cagacaaagg tacacatata tacacatgag ttcatgcgca cacacatgca tggacactta   2460
caaacgcctt cagagacaaa taggcataga cacacaacca ctcacagaaa cagataccaa   2520
tatgcatggt cctgtgtaca cagaaacaga ctataggcaa atatacacaa ataaactata   2580
tagatacaaa gatatgcata tacacacatg tacagaaaca tcttcacatg tgtacactaa   2640
catgtgaaca ggtatagcac acagatacac ctggactctg accagggctg taatctccaa   2700
ggctcacggc tcagagagcc tacactaggc tgggtcactg atactcctca ggagcccact   2760
ctatgattgg gagagataac cccaggtaca aagtatgcct atctgtctca acaccatggg   2820
gcagaagata ctccactaac cacccatgac agaaagttag ccttggctgt gtctccatta   2880
atagaacacc tcagaagacc aatgtgaaat tgcctaaccc actcacaccc accctgatct   2940
ccagttcaaa atgcagaaaa cataatgcag ttgtccaaaa gatgccccaa ccacacacac   3000
acacacacac acacacacac acacacacac acacacacac acacacacac accatcaagg   3060
agcctctgta aggagtcacc acccaataac actgcctctt tgggctcata tcctggacat   3120
tcttcatatt catatccatt tggggcctag gctttagata tccccaaggg ctcatcttta   3180
cagggatcag agatcccaat aaatgccctg gtcccacagc ctccctcagg tatctgtctg   3240
tttatctctt ggtaccaaga cccaacattg ctggcagggg taggacaagc aacgcacggg   3300
aactctgatc aaagaaagtc atgagatgcc tgagtccttc aggaagtaag gagggacaac   3360
ctctggtatc cctgttctta ttgctaaagc ccaagagaca gggagacctg ctctaaattc   3420
tcagtctaaa cagcaccgat ggcaccacct gctcagggaa agtccagagc acaccaatat   3480
cattttgcca cagttcctga gtctgccttt acccaggtcc atacattgca tctgtcttgc   3540
ttgctctgct gccccagggc tcctggaaca aaggctccaa attagtgtgt cctacagctt   3600
ggcctgttct gtgcctccgt ctagcttgag ctattagggg accagtcaat actcgctaag   3660
attctccaga accatcaggg caccccaacc cttatgcaaa tgctcagtca ccccaagact   3720
```

-continued

```
tggcttgacc ctccctctct gtgtcccttc atagaggggg aggtgaatgc tgaggaggaa   3780
ggctttgaga acctgtggac cactgcctcc accttcatcg tcctcttcct cctgagcctc   3840
ttctacagca ccaccgtcac cctgttcaag gtagtgtggt tgtggggctg aggacacagg   3900
gctgggacag ggagtcacca gtcctcactg cctctacctc tactccctac aagtggacag   3960
caattcacac tgtctctgtc acctgcaggt gaaatgactc tcagcatgga aggacagcag   4020
agaccaagag atcctcccac agggacacta cctctgggcc tgggatacct gactgtatga   4080
ctagtaaact tattcttacg tctttcctgt gttgccctcc agcttttatc tctgagatgg   4140
tcttctttct agactgacca aagacttttt gtcaacttgt acaatctgaa gcaatgtctg   4200
gcccacagac agctgagctg taaacaaatg tcacatggaa ataaatactt tatcttgtga   4260
actcacttta ttgtgaagga atttgttttg tttttcaaac ctttcctgcg gtgttgacag   4320
cccaaggatt atctgaatag agcttaggaa ctggaaatgg aacagtgcag tctgatggta   4380
cttaagggag aaagagggaa aggaggtgtg gaagaagaaa aaagagaagc agagggggag   4440
gggagaaggg agagggagag ggagagggag agggagaggg agagggagag ggagagagag   4500
agagagagag agagagagag agagagagag agagagcatg cactctaaca gcaaagtaca   4560
acacaggcag ccaatggata gcactctggt tatctaccct gatggaagaa gggaagtagg   4620
gcagagaaaa ttccaggcct aatctcccaa aagcaacaga acctggaaac tagcctctag   4680
ccttaggtct ctgctctgtc cccagcccac catcttgggc tggtgttgct tcaagctagt   4740
aatttaggtc ttatcccaaa gctttgtggt atgtgggtgt gcctttgggg agttggctga   4800
gattttgaag atgtttgtac ctctcccaca acatgacaag ccctaggggt tagtcaataa   4860
ctcaaattct ctgtctatga caactgctgt atgactatat gaagaaatgg gataaagatg   4920
ctatagtcac tc                                                       4932
```